US012272901B2

(12) United States Patent
Jiang

(10) Patent No.: US 12,272,901 B2
(45) Date of Patent: Apr. 8, 2025

(54) CONNECTING WITH A WIRE JOINT HAVING ROTATABLE HEAD

(71) Applicant: MEI HOSPITAL, UNIVERSITY OF CHINESE ACADEMY OF SCIENCES, Zhejiang (CN)

(72) Inventor: Longfu Jiang, Zhejiang (CN)

(73) Assignee: MEI HOSPITAL, UNIVERSITY OF CHINESE ACADEMY OF SCIENCES, Ningbo (CN)

( * ) Notice: Subject to any disclaimer, the term of this patent is extended or adjusted under 35 U.S.C. 154(b) by 468 days.

(21) Appl. No.: 17/859,042

(22) Filed: Jul. 7, 2022

(65) Prior Publication Data
US 2022/0336998 A1 Oct. 20, 2022

Related U.S. Application Data

(63) Continuation-in-part of application No. PCT/CN2020/142590, filed on Dec. 31, 2020.

(30) Foreign Application Priority Data

Jan. 7, 2020 (CN) .......................... 202020024478.9
Dec. 16, 2020 (CN) .......................... 202023031905.5

(51) Int. Cl.
*H01R 13/62* (2006.01)
*H01R 13/622* (2006.01)
(52) U.S. Cl.
CPC ....... *H01R 13/622* (2013.01); *H01R 2201/12* (2013.01)

(58) Field of Classification Search
CPC ....... H01R 13/622; H01R 13/62; H01R 13/60
See application file for complete search history.

(56) References Cited

U.S. PATENT DOCUMENTS 5,882,228 A * 3/1999 Kobler ................... H01R 24/46
439/620.05
6,530,085 B1 * 3/2003 Perlman ............. H04N 21/4334
439/502

(Continued)

FOREIGN PATENT DOCUMENTS

| CN | 205646265 U | 10/2016 |
| CN | 109529195 A | 3/2019 |
| CN | 209848150 U | 12/2019 |

*Primary Examiner* — Harshad C Patel

(57) ABSTRACT

The present invention discloses a connecting wire, which comprises an electric wire and a wire joint connected to the electric wire; further comprises a connecting piece arranged on the electric wire, the connecting piece can be simultaneously connected with at least two devices. Through the setting of the connecting piece, a plurality of devices can be connected simultaneously, without additional temporary processing of the connecting wire, avoiding excessive contact between the lead of the connecting wire and the outside, and reducing the interference of external signals on the signal transmission of the connecting wire, so that the ECG monitoring analyzer can monitor the intracavitary ECG and electrode impedance changes in a timely and accurate manner, to ensure that the electrode lead can be screwed into the patient's heart safely and accurately and the surgery can be completed better and more safely.

16 Claims, 11 Drawing Sheets

(56) References Cited

U.S. PATENT DOCUMENTS

| | | | | |
|---|---|---|---|---|
| 6,790,077 B1* | 9/2004 | Chen | H01R 31/06 | 439/502 |
| 7,057,108 B1* | 6/2006 | Sodemann | H01R 13/7135 | 439/639 |
| 7,121,852 B2* | 10/2006 | Ng | H01R 35/04 | 439/31 |
| 7,200,856 B2* | 4/2007 | Perlman | H04N 21/4112 | 439/502 |
| 7,285,021 B2* | 10/2007 | Bell | G06F 1/1632 | 439/505 |
| 7,841,903 B2* | 11/2010 | Saito | H01R 13/6675 | 439/638 |
| 8,033,860 B2* | 10/2011 | Milstein | H01R 31/02 | 439/502 |
| 8,210,868 B1* | 7/2012 | Robling | H01R 31/02 | 439/502 |
| 8,298,003 B2* | 10/2012 | Wu | H01R 27/02 | 439/501 |
| 8,376,782 B2* | 2/2013 | Govekar | H01R 25/006 | 439/502 |
| 8,382,533 B2* | 2/2013 | Pavlovic | H01R 13/187 | 439/840 |
| 8,513,554 B2* | 8/2013 | Peng | H01H 9/0228 | 200/332.1 |
| 8,517,772 B2* | 8/2013 | Wu | H01R 24/62 | 439/501 |
| 8,550,856 B2* | 10/2013 | Lin | H01R 31/06 | 439/638 |
| 9,257,758 B2* | 2/2016 | Kellman | H01R 4/20 | |
| 9,385,464 B2* | 7/2016 | Wu | H01R 27/00 | |
| 9,515,442 B2* | 12/2016 | Cymerman | H01R 13/64 | |
| 10,027,080 B2* | 7/2018 | Solland | H01R 29/00 | |
| 10,168,441 B1* | 1/2019 | Nicolas | G01V 1/202 | |
| 11,502,467 B2* | 11/2022 | Deng | H01R 31/06 | |
| 2006/0013410 A1* | 1/2006 | Wurtz | H04R 1/1033 | 381/74 |
| 2008/0194149 A1* | 8/2008 | Kim | H01R 27/02 | 439/639 |
| 2009/0113101 A1* | 4/2009 | Liu | H01R 31/06 | 710/300 |
| 2010/0215186 A1* | 8/2010 | Chang | H01R 31/02 | 381/74 |

* cited by examiner

CONNECTING WITH A WIRE JOINT HAVING ROTATABLE HEAD

CROSS REFERENCE TO RELATED APPLICATIONS

The present application is a Continuation-In-Part Application of PCT Application No. PCT/CN2020/142590 filed on Dec. 31, 2020, which claims the benefit of Chinese Patent Application Nos. 202020024478.9 filed on Jan. 7, 2020 and 202023031905.5 filed on Dec. 16, 2020. All the above are hereby incorporated by reference in their entirety.

FIELD OF THE INVENTION

The present invention belongs to the technical field of medical devices, particularly relates to a connecting wire.

BACKGROUND OF THE INVENTION

A pacemaker is an electronic therapy device implanted in the body. The pulse generator emits electrical pulses that are powered by batteries, and through the conduction of the lead electrodes, electrical pulses stimulate the myocardium that is in contact with the electrodes, to excite and contract the heart, so as to achieve the purpose of treating some cardiac dysfunctions caused by arrhythmias; one end of the electrode lead is the electrode end, which is used to connect the pacemaker, and the other end of the electrode lead is the screw-in end, which is used to implant the patient's heart, and both the electrode end and the screw-in end are provided with a cathode and an anode; since the anode of the electrode end is a ring structure, it is also called an anode ring.

During the operation, after the screw-in end of an electrode is placed into a patient's heart and adheres to the retroendomyocardium, a surgeon needs to rotate the electrode lead to screw the cathode of the screw head of the electrode lead into the myocardium; during the screwing process of the screw-in end, it is necessary to monitor the intracavity electrocardiogram and electrode impedance changes of the cathode end screwed under a pacing or non-packing state at any time using a ECG monitoring analyzer and a pacemaker programmer. Through observation on the changes of these parameters, surgeons can control the screw-in depth of the electrodes more accurately, so that the surgery can be completed more smoothly and safely.

In the prior art, the electrode end of the electrode lead needs to be connected with the ECG monitoring analyzer and the pacemaker programmer simultaneously; the electrode lead is connected with the ECG monitoring analyzer through an alligator clip of a connecting wire and another adapter cable; specifically, one end of the adapter cable is inserted into the intra-cavity signal junction box of the ECG monitoring analyzer, and the insulating outer skin on the other end of the adapter cable is peeled off to expose the metal, and then the alligator clip of the connecting wire is clamped on the peeled metal, to realize the connection of the alligator clip with the adapter cable, then the electrode lead is connected to the connecting wire, so that the intracardiac electrical signal is connected to the ECG monitoring analyzer through the integrated intracavity signal junction box; then the alligator clip on the built-in connecting wire of the pacemaker programmer is clamped on the peeled metal of the adapter cable, to realize the connection between the motor lead, the connecting wire and the pacemaker programmer; however, this connection method is easily interfered by the external signals due to no barrier of outer skin. The signal transmission of the connecting wire is very unstable, which affects the detection accuracy of the ECG monitoring analyzer, making it difficult for the surgeon to accurately grasp whether the screw-in end has reached the appropriate site.

SUMMARY OF THE INVENTION

The present invention provides a connecting wire with stable signal transmission.

In order to achieve the above object, the present invention adopts the following technical solutions: a connecting wire, comprising an electric wire and a wire joint connected to the electric wire; wherein the connecting wire further comprise a connecting piece arranged on the electric wire, the connecting piece can be simultaneously connected with at least two devices; through the setting of the connecting piece, a plurality of devices can be connected simultaneously, without additional temporary processing of the connecting wire, avoiding excessive contact between the lead of the connecting wire and the outside, and reducing the interference of external signals on the signal transmission of the connecting wire, so that the ECG monitoring analyzer can monitor the intracavitary ECG and electrode impedance changes in a timely and accurate manner, to ensure that the electrode lead can be screwed into the patient's heart safely and accurately and the surgery can be completed better and more safely.

Further, the connecting piece comprises a wiring portion connected to the electric wire, a first connection portion connected to the wiring portion, and a second connection portion connected to the wiring portion; through the setting of connecting pieces, multiple devices can be connected separately, avoiding being connected in one place simultaneously and causing signal interference, further ensuring that the connecting wire can transmit signals in a timely and stable manner and guarantee the accuracy of the signal transmission.

Further, the first connection portion is provided with an exposed portion for conducting electricity; through the setting of the exposed portion on the first connection portion, the connection, clamping and fixing of the alligator clip can be facilitated, and the occurrence of relative rotation or disconnection after displacement at the connection between the alligator clip and the first connection portion is reduced when the screw-in end of the electrode lead is screwed in, further ensuring the stable transmission of signals of the connecting wire.

Further, an insertion slot is provided on the second connection portion; through the setting of the insertion slot, the connecting wire can be quickly inserted on the pacemaker programmer, which facilitates the fast connection and fixing between the devices through the connecting wire, thereby improving the conveniences for the use, connection and replacement of connecting wire; meanwhile, the insertion slot is inserted into the terminal of the pacemaker programmer to reduce the contact area with the outside, thereby further reducing the interference of external signals on the transmission signal in the connecting wire, ensuring that the connecting wire can transmit signals in a timely and stable manner and guarantee the accuracy of the signal transmission.

Further, the first connection portion on the connecting piece can form a plug fit with the insertion slot on the adjacent connecting piece; through the setting of plug fit of the connecting piece, the signals of multiple devices can be connected to the same port simultaneously, which facilitates the operation of a specific program and the synchronous control of the corresponding equipment, and also facilitates surgeons to conduct testing on the equipment according to the operation of the specific program, thereby ensuring the normal operation of equipment during the operation and facilitating the completion of operation in a safe and accurate manner.

Further, a connecting rod is provided in the insertion slot, and a connecting hole matched with the connecting rod is provided on the first connection portion; through the setting of the connecting rod and the connecting hole, the adjacent connecting pieces can be positioned, connected and matched quickly and accurately, improving the convenience for the use of connecting wire and the stability of the connection.

Further, the electrode lead is used for connecting with the wire joint; when the electrode lead rotates, at least part of the wire joint can rotate with the rotation of the electrode lead. Through the setting of the wire joint, the electrode end of the electrode lead can be connected with the wire joint, thus, when a surgeon rotates the electrode lead during the operation, at least part of the wire joint can rotate synchronously with the rotation of the electrode lead, and the electrode lead will not be twisted and knotted. The surgeon does not need to remove the electrode end from the alligator clip to untie the twisted and knotted part, and the assistant does not need to rotate the electrode end connected to the alligator clip. The operation is more convenient and guarantees that the wire joint can conduct electrical signals to the ECG monitoring analyzer and pacemaker programmer in a real-time, continuous, stable and accurate manner. Thus, it ensures that the surgeon can grasp the changes of ECG and electrode impedance in real time, and accurately judge whether the screw-in end reaches the site or whether the gap is broken through when screwing in, so as to ensure the accuracy of the screw-in site and reduce the patient's pain; and the operation can be completed more quickly, with a higher success rate; furthermore, because the electrode end is no longer clamped and fixed by the alligator clip, it will not cause damage to the electrode end, and the connection between the electrode lead and the pacemaker is more stable, ensuring that the pacemaker can always play the role of stably assisting in the patient's cardiac pacing.

Further, the wire joint comprises a rotatable head that can rotate back and forth and a rotating connecting portion for connecting with the electrode lead; the rotating connection portion is provided on the rotatable head; through the setting of the above structure, the electrode lead can be connected to the rotatable head on the wire joint through the rotating connecting portion, thus, when the electrode lead rotates, the rotatable head can rotate with the rotation of the electrode lead, achieving the purpose of preventing the electrode lead from being twisted and knotted.

Further, the wire joint also comprises an elastic piece matched with the electrode lead, which makes the connection more stable and ensures more stable transmission of electrical signals; the data displayed on the ECG monitoring analyzer and pacemaker programmer are more accurate, so that the surgeon can better control the situation and make the operation proceed more smoothly.

Further, the wire joint also comprises a connecting head for connecting the rotatable head and the electric wire, which ensures the stable transmission of electrical signals and makes the surgeon monitor the patient's conditions better, to find the correct site more rapidly and accurately.

In summary, in the present invention, through the setting of the wire joint, the electrode lead will not be twisted and knotted, so that the changes of ECG and electrode impedance can be detected in a real-time, continuous and accurate manner during the operation, and the surgeon can complete the operation more smoothly, with a lower risk and a higher success rate.

DETAILED DESCRIPTION

Figure 1:
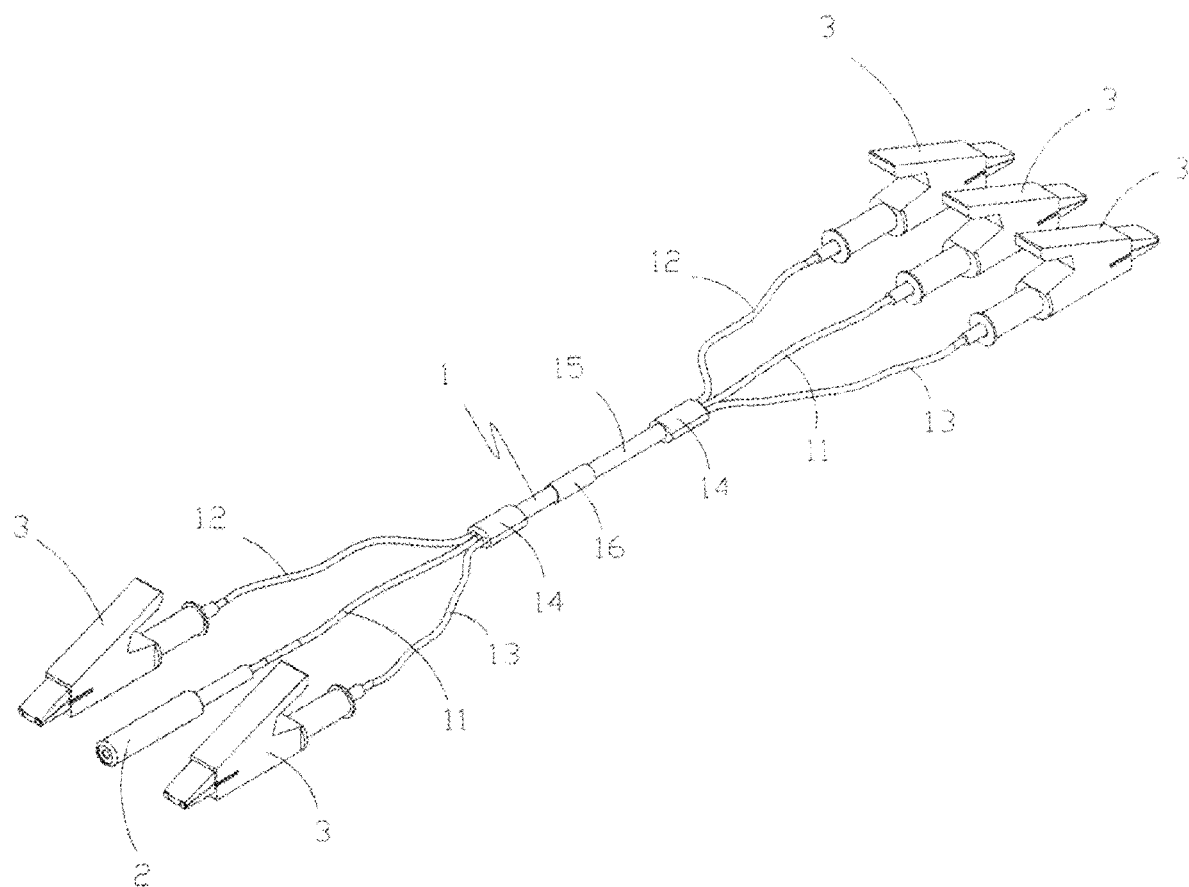
FIG. 1 is a schematic diagram of a three-dimensional structure of Example 1 of the present invention.
Figure 2:
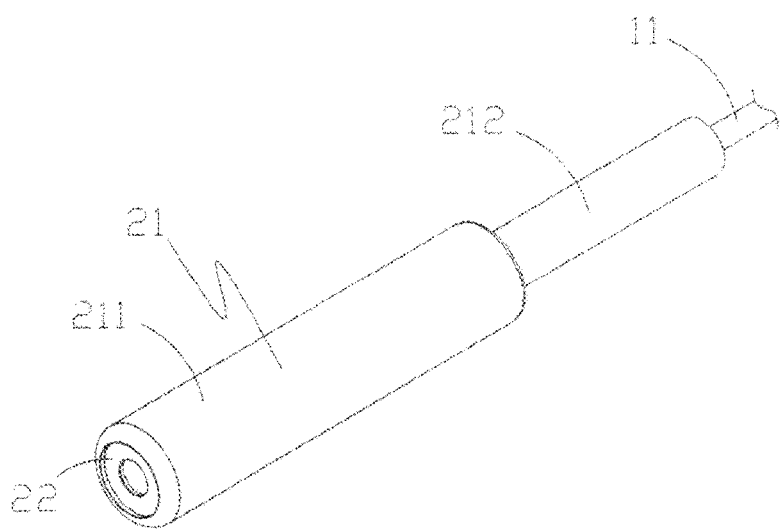
FIG. 2 is a schematic diagram of a three-dimensional structure illustrating the matching of a wire joint and an electric wire in FIG. 1.
Figure 3:
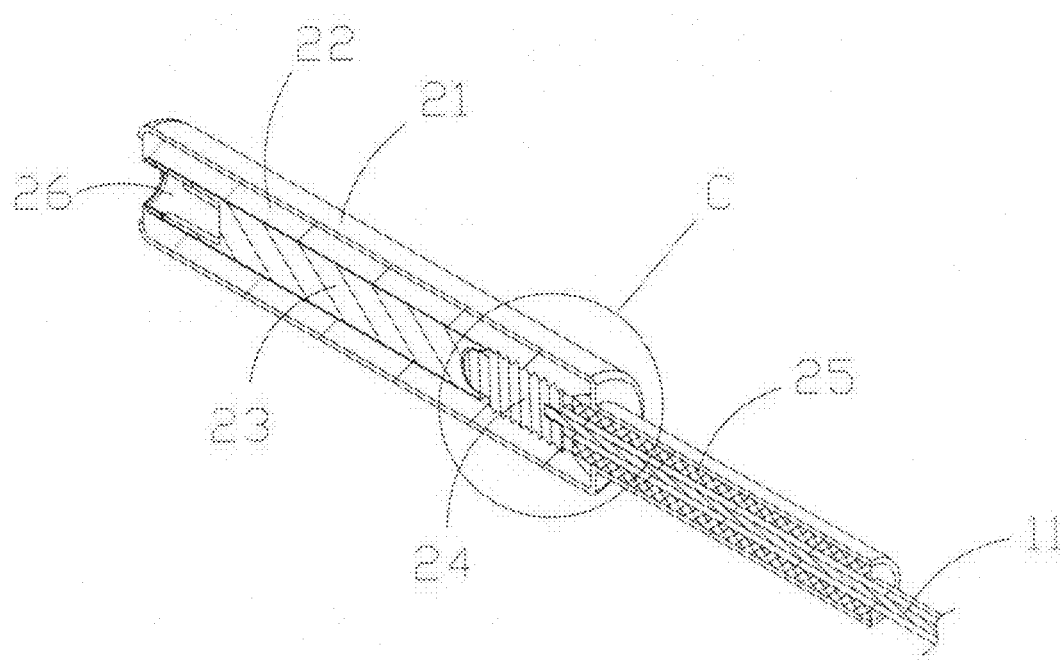
FIG. 3 is a cross-sectional view of a three-dimensional structure illustrating the matching of a wire joint and an electric wire in FIG. 1.
Figure 4:
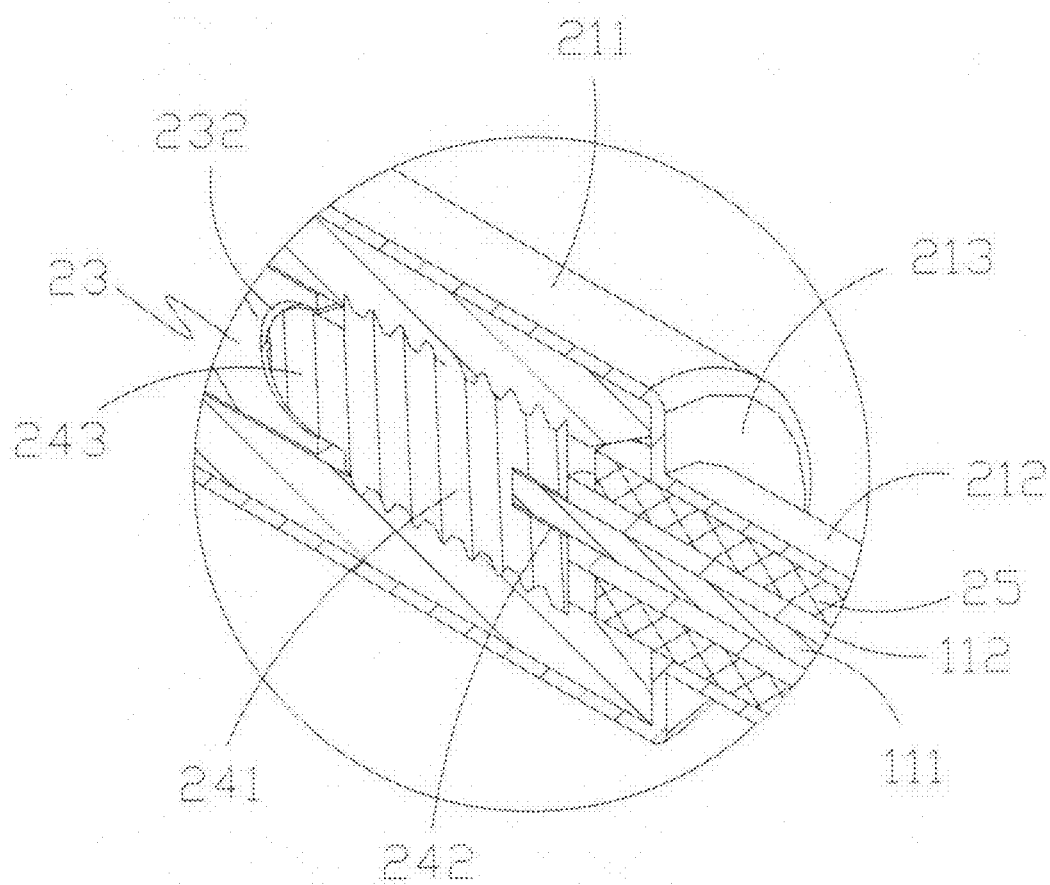
FIG. 4 is an enlarged schematic diagram of C in FIG. 3.
Figure 5:
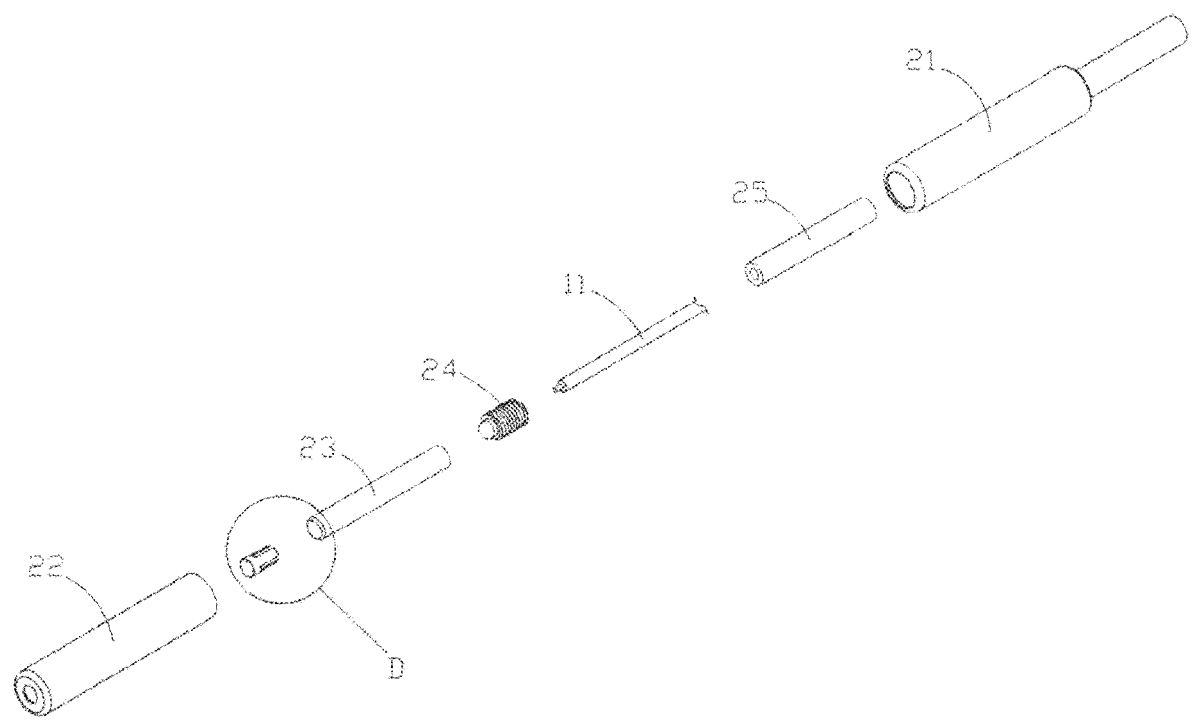
FIG. 5 is an exploded view illustrating the matching of a wire joint and an electric wire in FIG. 1.
Figure 6:
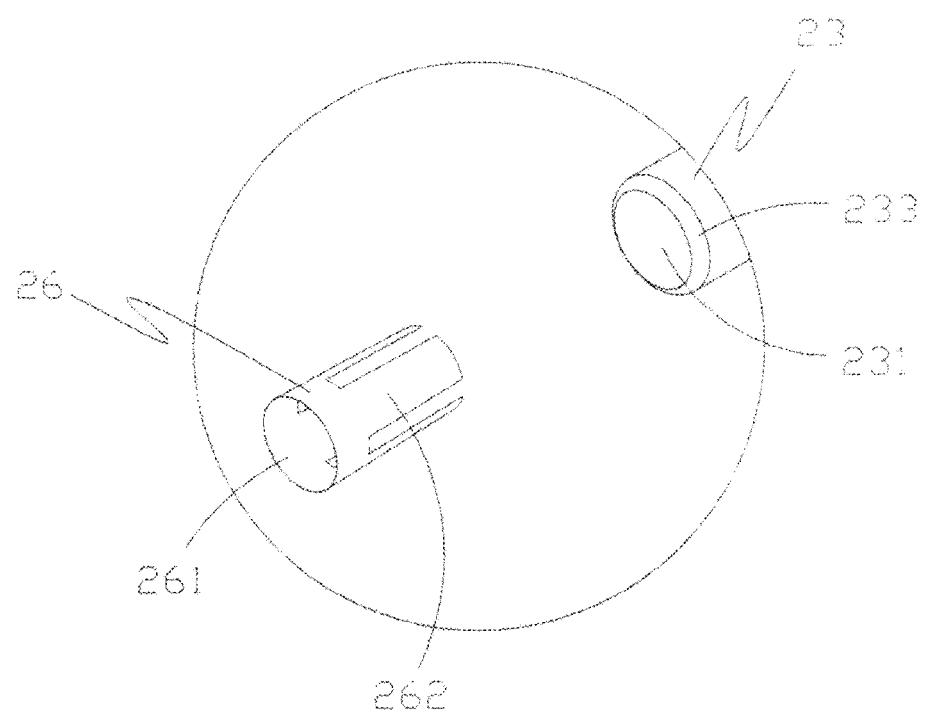
FIG. 6 is an enlarged schematic diagram of D in FIG. 5.
Figure 7:
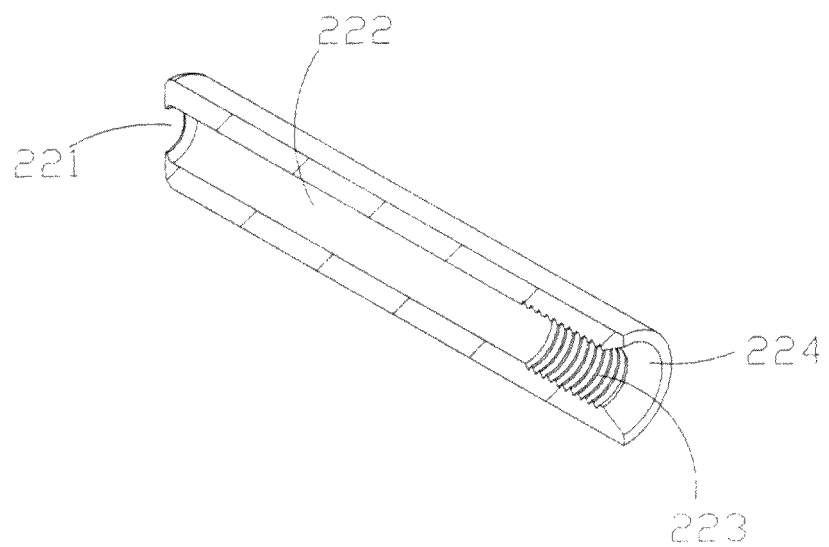
FIG. 7 is a cross-sectional view of a three-dimensional structure of a casing in FIG. 1.
Figure 8:
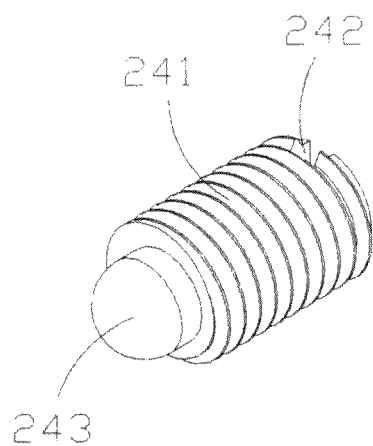
FIG. 8 is a schematic diagram of a three-dimensional structure of a connecting head in FIG. 1.

A plurality of preferred embodiments of the present invention will be described with reference to the companying drawings, so that the technical contents are more accurate and easier to understand. The present invention can be embodied in many different forms of embodiments, and the protection scope of the present invention is not limited to the embodiments mentioned herein.

Example 1

As shown in FIGS. 1 to 8, a connecting wire comprises a wire joint 2, an alligator clip 3 and an electric wire 1, wherein the electric wire 1 comprises a first lead 11, a second lead 12, a third lead 13, a hub joint 14, a hub 15, a standard jacket 16 and a wire jacket 17; the diameter of the first lead 11 is 1 mm-2 mm, preferably 1.5 mm±0.05 mm; the first lead comprises a conductive core 111 and an insulating layer 112, the conductive core is made of copper or other conductive materials. The material adopted in this example is 60/0.08TC (tinned copper wire), the insulating layer 112 is covered on the outside of the conductive core, is formed in a tubular structure, and is made of PVC; the second lead 12 and the third lead 13 have the same size and structure as those of the first lead 11; a wire jacket 17 is sleeved on the first lead, the second lead and the third lead, and the wire jacket is made of silicone material or other materials that meet the medical standards; since the gap between the outer wall of the lead and the inner wall of the connecting ring is filled by the wire jacket, the wire jacket is made of silicone, and the insulating layer is made of PVC, with a large friction between them, when the lead is pulled away from the alligator clip by an external force, the wire jacket plays the role of sharing the external force exerted on the lead, so that the connection and fixation between the lead and the alligator clip is not easily damaged, ensuring that they are always in a stable electrical connection state, thereby improving the stability of data transmission, making the detected data more accurate and making the operation safer with a higher success rate.

Further, the hub joint 14 is mounted on the outer side of the first lead, the second lead and the third lead, and plays the role of bundling the three leads into one, so that the three leads and the alligator clip and wire joint connected to the three wires are not easily twisted and knotted, and more convenient to use, avoiding the problem of the time consuming for arranging the leads, saving the time for the operation, and further improving the success rate of the operation. The hub joint is made of 25P black PVC material, which conforms to the RoHS directive. The hub 15 is made of wear-resistant medical PVC material, which is sleeved on the outer side of the first lead, the second lead and the third lead after being bundled, preferably directly injection molded on the outer side of the leads, playing a role of preventing the leads, alligator clip and wire joint from knotting; the standard jacket is sleeved on the outer side of the hub, which facilitates to make some logos or other prompt text thereon.

Further, one end of the first lead 11 is electrically connected to the alligator clip 3, and the other end is electrically connected to the wire joint 2; both ends of the second lead 12 and the third lead 13 are electrically connected to the alligator clip 3; the wire joint 2 on the first lead 11 is used to connect with the electrode lead of the pacemaker, and the alligator clip on the other end of the first lead is used to connect with the ECG monitoring analyzer and/or the pacemaker programmer; the alligator clip 3 on one end of the second lead 12 is used to hold the patient's skin as an anode, and the alligator clip on the other end is connected to the ECG monitoring analyzer and/or the pacemaker programmer; the alligator clips at both ends of the third lead 13 are used as spare parts. During the monitoring process, depending on different situations, the alligator clip on one end of the third lead can be chosen to clamp the anode ring of the electrode end, and the alligator clip on the other end is connected to the ECG monitoring analyzer and the pacemaker programmer, to obtain more implantation parameters.

In other embodiments, the lead segments of the first lead 11 and the third lead 13 located in the hub 15 are integrated into one, so that the electrical signals of the two can communicate with each other; that is, the first lead 11 and the third lead 13 may be two sub-wires or four wire ends branched from the same lead.

In order to facilitate the distinction, the insulating layer of the three leads, the clip cover on the alligator clip and the outer skin on the wire joint are produced in different colors, wherein, the first lead and the wire joint and alligator clip thereon are all black; the second lead is white and the alligator clip thereon is yellow; the third lead and the alligator clip thereon are all red.

Specifically, the wire joint 2 comprises an outer skin 21, a casing 22, a rotatable head 23, a connecting head 24 and a middle sleeve 25; the casing 22 is made of a metal material, has electrical conductivity, and is formed in a hollow cylindrical structure. One end of the casing is provided with a socket 221, an accommodating cavity 222 is formed in the middle part, and an interface 223 is formed on the other end; the rotatable head 23 is made of a conductive metal material, and a copper material is adopted in this example. The rotatable head is formed in a cylindrical structure, and the rotatable head is mounted in the accommodating cavity 222. The rotatable head can rotate in the accommodating cavity, and the outer surface of the rotatable head is always in contact with the cavity wall of the accommodating cavity, so as to realize the rotating electrical connection between the rotatable head and the casing; a rotating connecting portion 231 is formed on the end of the rotatable head close to the socket 221. In this example, the rotating connecting portion is a slot; preferably, the inner diameter of the rotating connecting portion 231 is the same as the inner diameter of the socket 221, so that the electrode end connected with the electrode lead and the pacemaker can pass through the socket 221 to connect with the rotating connecting portion 231, and meanwhile the edge of the socket can play an auxiliary fixing role for the electrode end, to prevent the electrode end from being deflected, stabilizing the mounting.

Further, an elastic piece 26 is mounted in the rotating connecting portion 231. The elastic piece is made of metal material and has certain elasticity. In this example, brass is used; in other examples, it may be made of other metal materials with electrical conductivity and elasticity; the elastic piece comprises a first fixing portion 261 and a second fixing portion 262, the first fixing portion is formed in a ring structure, and its outer diameter is slightly larger than the inner diameter of the rotating connecting portion 231, thus, when the elastic piece is mounted into the rotating connecting portion, the first fixing portion and the rotating connecting portion can form an interference fit, and the mounting is more stable; furthermore, after the electrode end of the electrode lead is inserted, the electrode lead can drive the elastic piece and the rotatable head to rotate together when rotating, while the elastic piece is difficult to rotate relative to the rotatable head, which makes more stable transmission of electrical signals; the second fixing portion is formed by at least part of the side of the first fixing portion extending outwardly in an arc-shaped sheet structure; and the diameter of the second fixing portion gradually decreases from the end close to the first fixing portion to the end away from the first fixing portion. A plurality of second fixing portions are arranged in a claw-like structure; when mounting the elastic piece, the second fixing portion orients the rotating connecting portion, and then the elastic piece is placed into the rotating connecting portion, thus, after the electrode end of the electrode lead is inserted into the rotating connecting portion, the second fixing portion can be closely attached to the surface of the electrode end, and under the elastic force of the second fixing portion, the electrode end can be clamped and fixed in the rotating connecting portion, the connection is more stable and is not easy to fall off; and meanwhile, the electrode end and the rotatable head can always maintain an electrical connection state, thereby making the transmission of electrical signals more stable and accurate, and providing reliable data support for the surgeon; Furthermore, the electrode end is not easy to rotate relative to the elastic piece, which avoids the electrode end from being worn, thus ensuring a stable connection between the electrode end and the pacemaker, so that the pacemaker and the electrode lead can always assist the patient in cardiac pacing stably. When the rotary head is accidentally stuck and cannot be rotated relative to the casing, the electrode end can rotate relative to the elastic piece due to the elasticity of the elastic piece, thus avoiding damage to the rotary head or the electrode lead; after the elastic piece 26 is mounted in the rotating connecting portion 231, the rotating connecting portion is closed up to form a closed edge 233 at the edge of the socket, thereby fixing the elastic piece in the rotating connecting portion, preventing the elastic piece from coming off as the electrode end is pulled out.

Preferably, a third fixing portion is also formed on the elastic piece 26. The third fixing portion is a convex portion formed by at least part of the inner surface of the elastic piece extending outwardly, so that the contact between the elastic piece and the electrode end is tighter, and the effect of fixing the electrode end is better.

Further, the connecting head 24 comprises a connecting column 241, a connecting groove 242 and a connecting convex portion 243. The connecting column 241 is made of a metal material with good electrical conductivity, and an external thread is provided on its outer surface, and a corresponding internal thread is provided in the interface 223. Therefore, the connecting head can be mounted in the interface to realize the threaded connection between the connecting head and the casing; the connecting groove 242 is formed on one end of the connecting column in a straight-line structure, which can not only facilitate the screwing of the connecting column into the interface, but also facilitate the electrical connection between the connecting head and the electric wire 1; the connecting convex portion 243 is provided on the other end of the connecting column, and is formed by at least part of the surface of the end of the connecting column extending outwardly; the end of the rotatable head 23 close to the interface 223 is provided with a rotating groove 232, when the rotatable head is mounted in the casing, and the connecting head and the casing are screwed together, the connecting convex portion 243 is just embedded in the rotating groove 232, to fit each other. The connecting convex portion can be rotated in the rotating groove, and the outer surface of the connecting convex portion is always in contact with the wall of the rotating groove, so as to realize the rotation and matching by electrical connection between the connecting head and the rotatable head.

Preferably, the rotating groove is provided in a flared structure, so that part of the outer surface of the connecting convex portion can always be in contact with the wall of the rotating groove, and the rotatable head is fixed in the accommodating cavity 222, and there is a gap between the connecting convex portion and the rotating groove, to prevent the rotatable head from moving in the axial direction of the casing, so that the connection between the rotatable head and the electrode end of the electrode lead is more stable, and the fixing force of the connecting head to the rotatable head can be easily adjusted, making the rotatable head to be mounted stably, without affecting the rotation of the rotatable head; furthermore, the contact area between the connecting convex portion and the rotatable head is always relatively constant, which makes the data transmission more stable, so that the change of the electricity and electrode impedance in the operation center can be accurately transmitted to the ECG monitoring analyzer and the programmer in a real-time and accurate manner, the surgeon can understand the various data parameters in the operation more clearly and accurately to better control the operation status, reduce the surgical risk and increase the success rate of surgery.

Further, the middle sleeve 25 is sleeved on the outer side of the first lead 11, and located on the side where the first lead is connected with the wire joint 2, to replace the wire jacket 17. The middle sleeve 25 is made of plastic material, which has certain elasticity and higher hardness than the rubber; after the first lead and the connecting head 24 are electrically connected and fixed, the middle sleeve is pushed into the flared segment 224 on the casing 22 along the first lead, so that the connection between the first lead and the connecting head is not easy to move with the movement of the wire joint, thereby ensuring the stability of the connection between the first lead and the connecting head and making more stable transmission of the electrical signals.

Further, the outer skin 21 is made of medical silicone material or other insulating materials, the outer skin comprises a first segment body 211, a second segment body 212 and a third segment body 213, the first segment body 211 is wrapped on the outer side of the casing 22, and the second segment body 212 is wrapped on the outer side of the middle sleeve 25, and the third segment body is used to connect the first segment body and the second segment body, so that the middle sleeve is stably mounted in the flared segment, and the middle sleeve will not rotate relative to the casing, thus the connecting head can be fixed at the preset position, and there will be no problem of loosening with the rotation of the rotatable head, which further ensures the stability of the connection between the rotatable head and the connecting head.

Example 2

Figure 9:
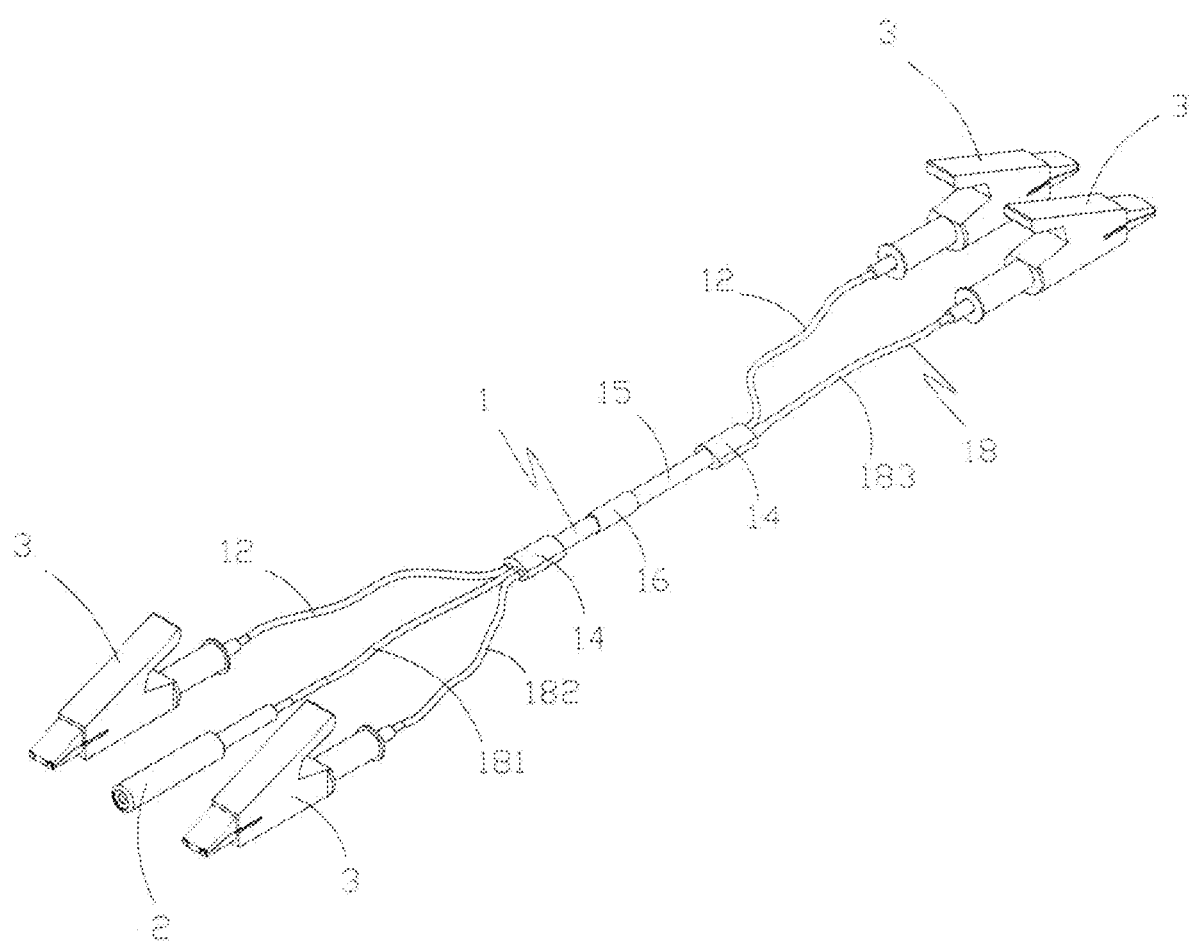
FIG. 9 is a schematic diagram of a three-dimensional structure of Example 2 of the present invention.

As shown in FIG. 9, the differences between this example and Example 1 are as follows: the first lead 11 and the third lead 13 are combined into one lead, which is called a busbar 18, and one end of the busbar is divided into a first sub-wire 181 and a second sub-wire 182, the first sub-wire is connected with the wire joint 2, the second sub-wire is connected with an alligator clip 3, and the other end of the busbar is a third sub-wire 183, and the third sub-wire is connected with an alligator clip 3.

Example 3

Figure 10:
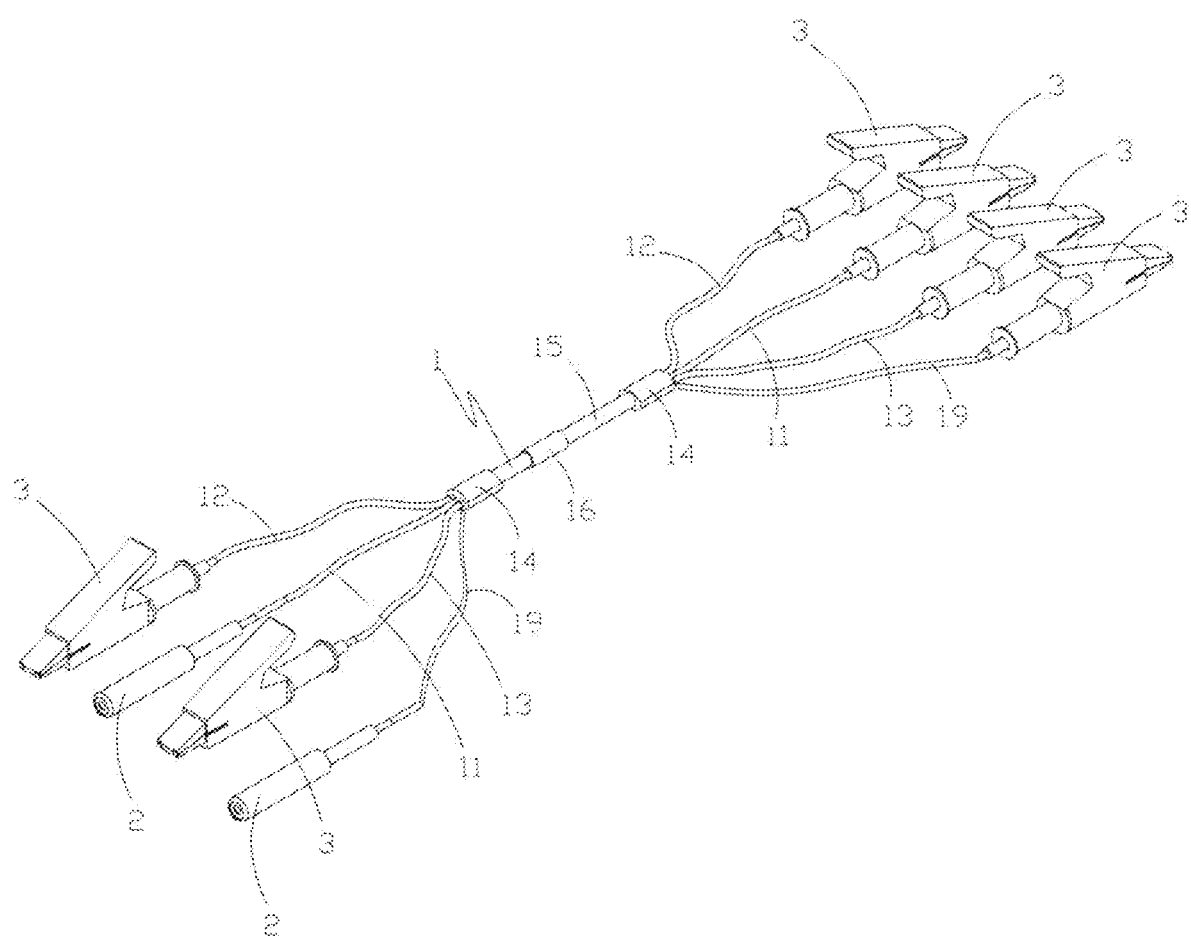
FIG. 10 is a schematic diagram of a three-dimensional structure of Example 3 of the present invention.
Figure 11:
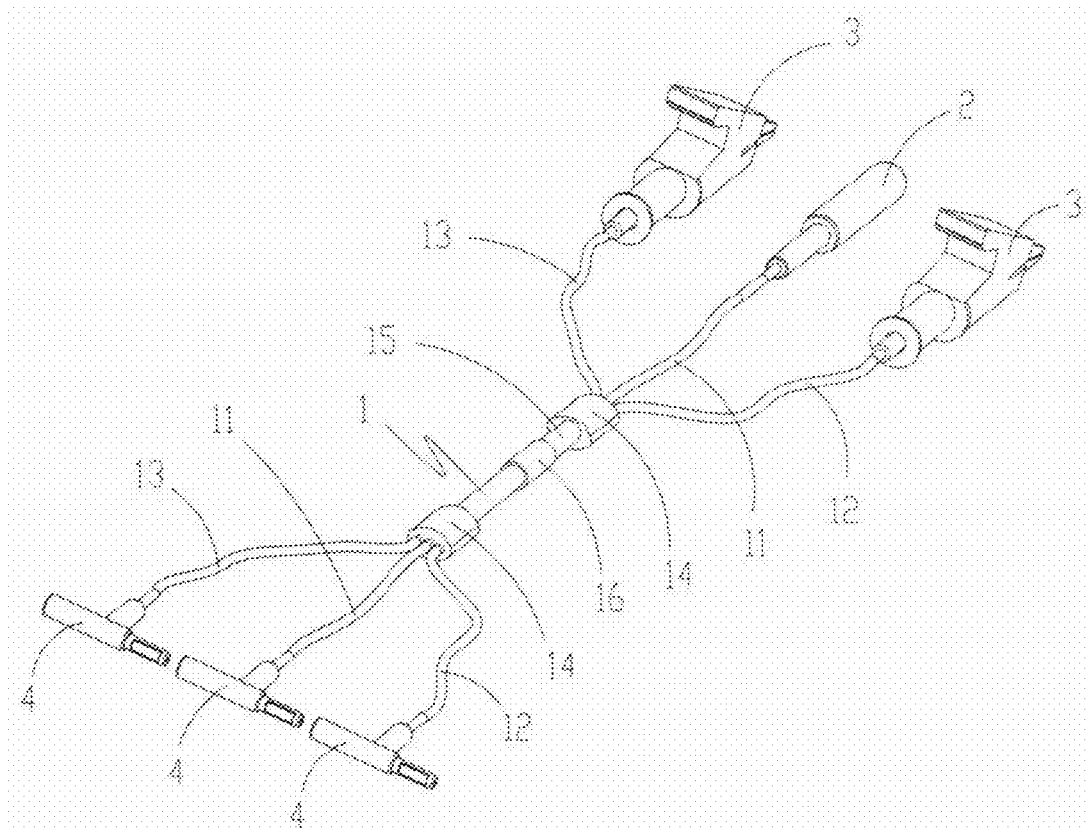
FIG. 11 is a schematic diagram of a three-dimensional structure of Example 4 of the present invention.
Figure 12:
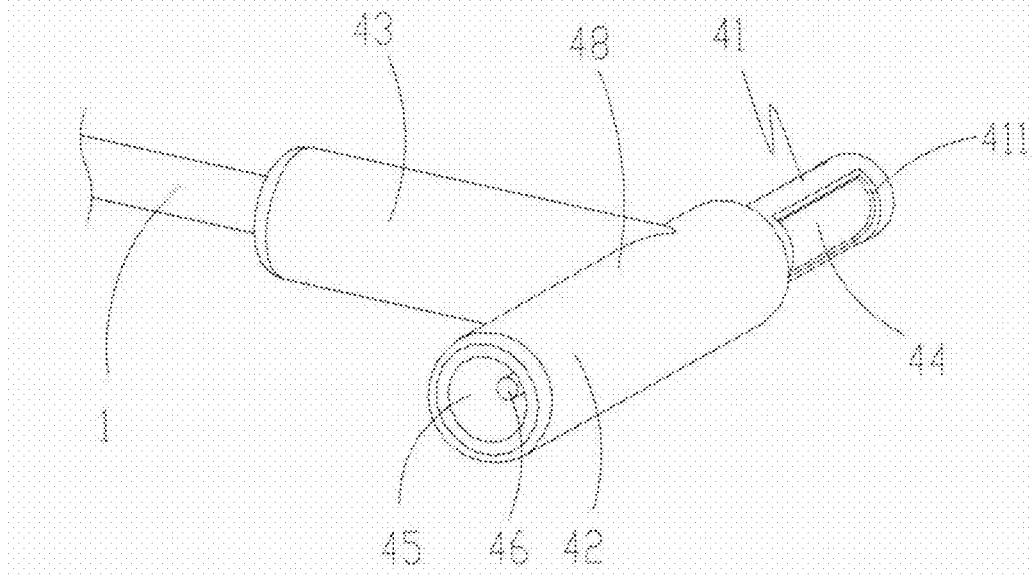
FIG. 12 is a schematic diagram illustrating the matching of a connecting piece and an electric wire in FIG. 11.
Figure 13:
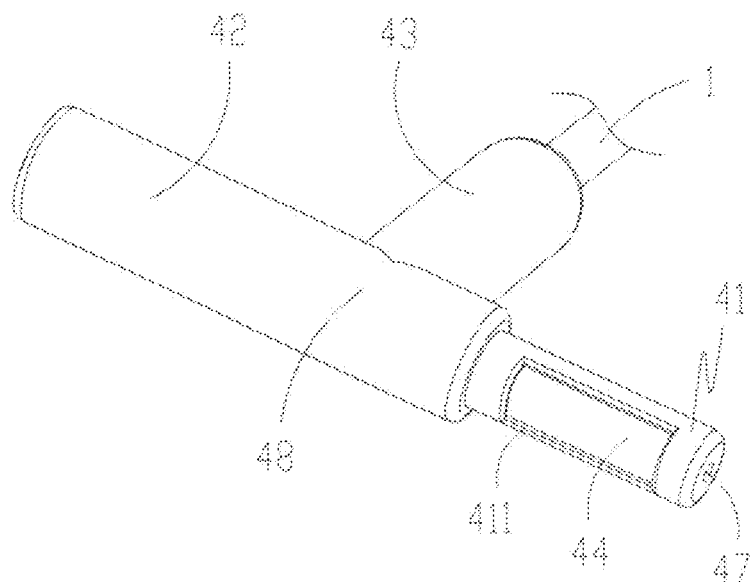
FIG. 13 is a schematic diagram illustrating the matching of a connecting piece and an electric wire from another perspective in FIG. 11.
Figure 14:
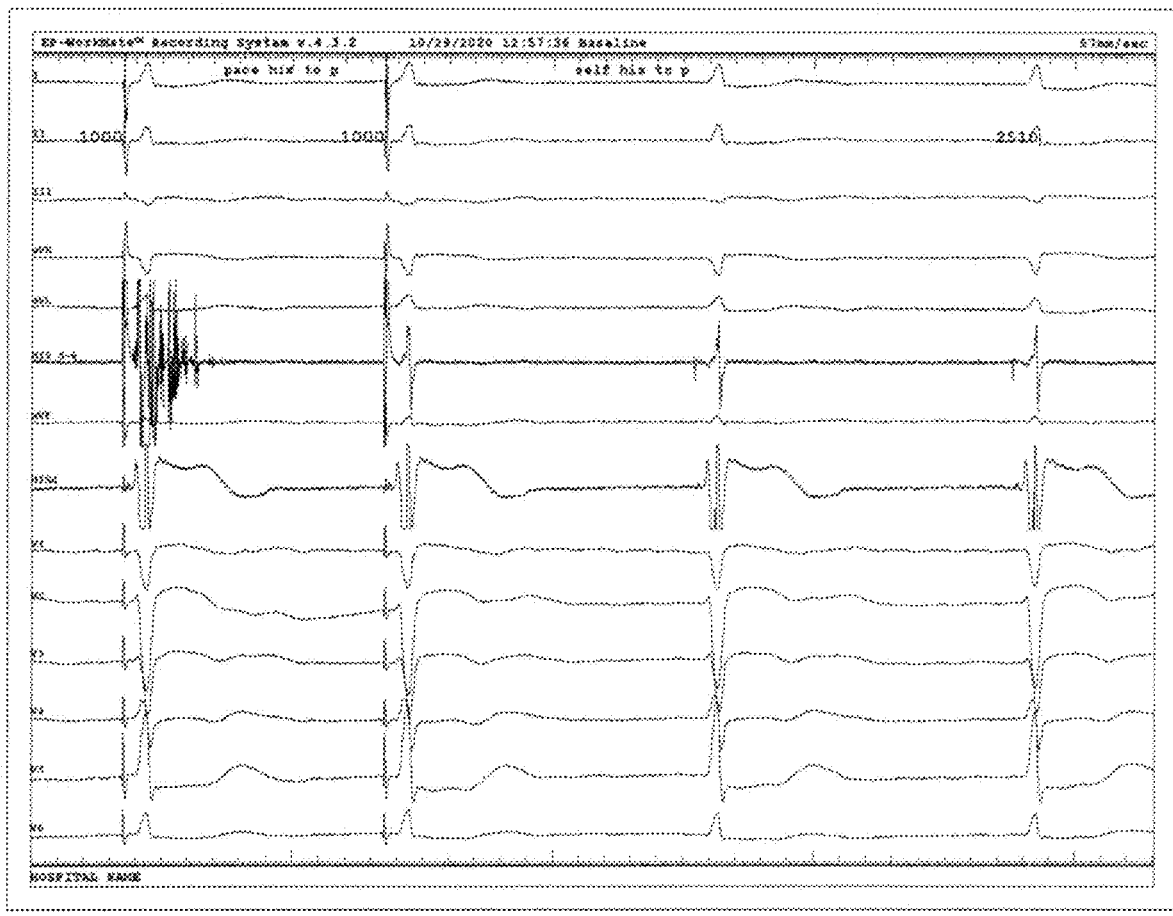
FIG. 14 is an intracavitary electrocardiogram displayed by an ECG monitoring analyzer in the mode of FIG. 11.

As shown in FIG. 10, the differences between this example and Example 1 are as follows: the electric wire 1 also comprises a fourth lead 19, and the fourth lead is also wrapped by the hub joint 14 and the hub 15, one end of the fourth lead is connected with the wire joint 2, and the other end is connected with an alligator clip 3; that is, the first lead and the fourth lead are connected with the same components, and the second lead and the third lead are connected with the same components, which match with each other to form two groups, facilitating the use of the two-electrode method.

Example 4

As shown in FIGS. 11 to 14, the differences between this example and Example 1 are as follows: in order to facilitate the connection during use, the three alligator clips 3 on the side where the wire joint 2 is not mounted on the connecting wire are replaced by connecting piece 4. The connecting piece 4 comprises a wiring portion 43, a first connection portion 41 and a second connection portion 42; the second connection portion can be directly connected with the intracavity signal junction box of the ECG monitoring analyzer, and the second connection portion is connected with the pacemaker programmer; through the setting of the first connection portion and the second connection portion, two devices can be connected at the same time, without the need for additional temporary secondary processing of the connecting wire, reducing the excessive contact between the leads of the connecting wire and the outside, reducing the interference of external signals on the signal transmission of the connecting wire; thus, the ECG monitoring analyzer can monitor the intracavity ECG and the electrode impedance changes in a timely and accurate manner, ensure the electrode lead can be screwed into the patient's heart safely and accurately, so that the operation can be completed more successfully and safely.

Further, the connecting piece 4 is covered with a shell 48, and the shell is made of insulating material, which can be made of plastic, silicone or other materials; through the setting of the insulating shell, the conductive material in the connecting piece can be connected to the outside world. Isolation, reducing external signal interference, connecting wire can transmit signals in a timely and stable manner and ensure the accuracy of signal transmission.

Further, the wiring portion, the first connection portion and the second connection portion are integrally consolidated and arranged in a "T" shape. The first connection portion and the second connection portion are respectively arranged on both sides of the wiring portion and are connected with the electric wire in the wiring portion; the first connection portion and the second connection portion are arranged on both sides of the wiring portion, which facilitates the connection and avoids the mutual interference of signals between the two first connection portions and the second connection portion, further ensuring that the connecting wire can transmit signals in a timely and stable manner and guarantee the accuracy of the signal transmission.

Further, two exposed holes 411 are formed on the side wall of the shell 48 at the first connection portion 41, so that an exposed portion 44 is formed on the first connection portion 41, and the inner metal is exposed, thus, the alligator clip can be directly clamped on the exposed portion, forming electric connection with the exposed metal; a connecting hole 47 is formed on the end of the first connection portion; the alligator clip on the built-in lead of the pacemaker programmer can be clamped on the exposed portion, which can facilitate the connection between the connecting wire and the pacemaker programmer, and further ensure the stable transmission of the signals of the connecting wire.

Further, an insertion slot 45 is formed on the second connection portion 42, and the insertion slot is provided with a connecting rod 46, so that the second connection portion can be directly connected to the intracavity signal junction box on the ECG monitoring analyzer, without the need for an adapter cable, which is convenient and fast, reducing the external interference, and further reducing the interference of external signals on the transmission signal in the connecting wire, ensuring that the connecting wire can transmit signals in a timely and stable manner and guarantee the accuracy of the signal transmission.

Further, the first connection portion on the connecting piece can also form a plug fit with the second connection portion of another adjacent connecting piece. Specifically, the first connection portion is correspondingly inserted into the insertion slot 45 of the other connecting piece, and at the same time, the connecting rod 46 can be inserted into the connecting hole 47, so that it can meet different usage requirements and is more practical.

Example 5

Figure 15:
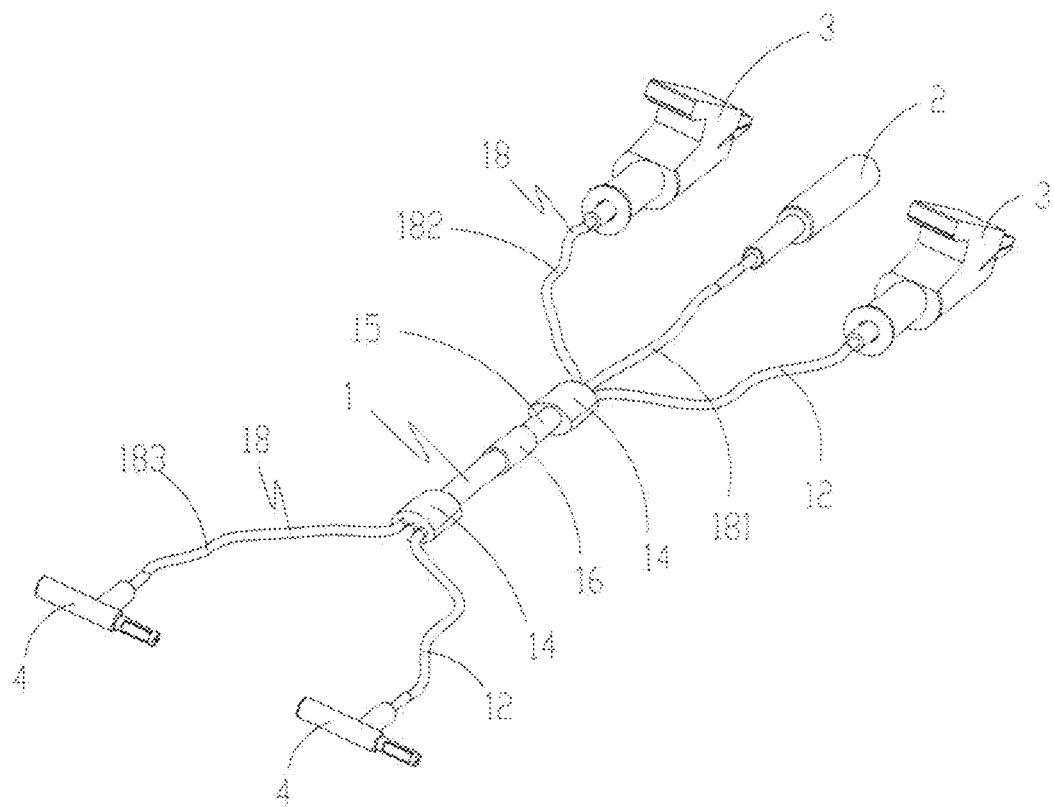
FIG. 15 is a schematic diagram of a three-dimensional structure of Example 5 of the present invention.

As shown in FIG. 15, the differences between this example and Example 4 are as follows: the first lead 11 and the third lead 13 are combined into one lead, which is called busbar 18, and one end of the busbar is divided into a first sub-wire 181 and a second sub-wire 182, the first sub-wire is connected with wire joint 2, the second sub-wire is connected with alligator clip 3, and the other end of the busbar is third sub-wire 183, and the third sub-wire is connected with a connecting piece 4.

Example 6

Figure 16:
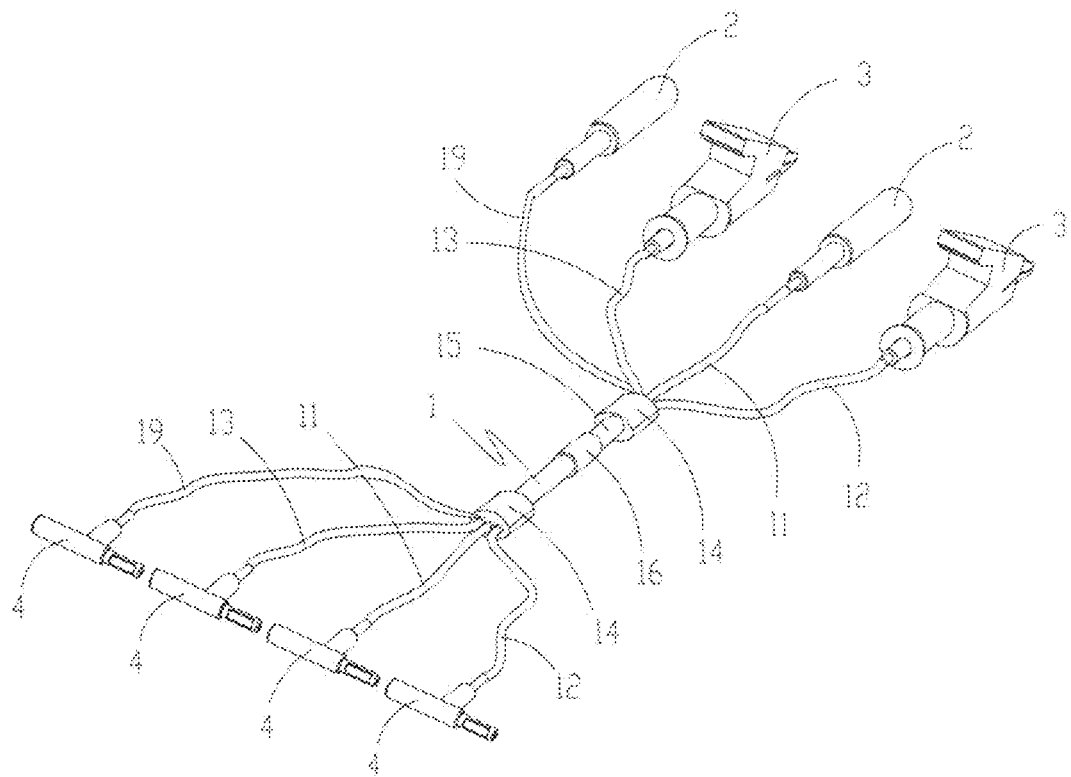
FIG. 16 is a schematic diagram of a three-dimensional structure of Example 6 of the present invention.

As shown in FIG. 16, the differences between this example and Example 4 are as follows: the electric wire 1 also comprises a fourth lead 19, the fourth lead is also wrapped by the hub joint 14 and the hub 15, one end of the fourth lead is connected with the wire joint 2, and the other end is connected with the connecting piece 4; that is, the first lead and the fourth lead are connected with the same components, and the second lead and the third lead are connected with the same components, which match with each other to form two groups, facilitating the use of the two-electrode method.

Example 7

Figure 17:
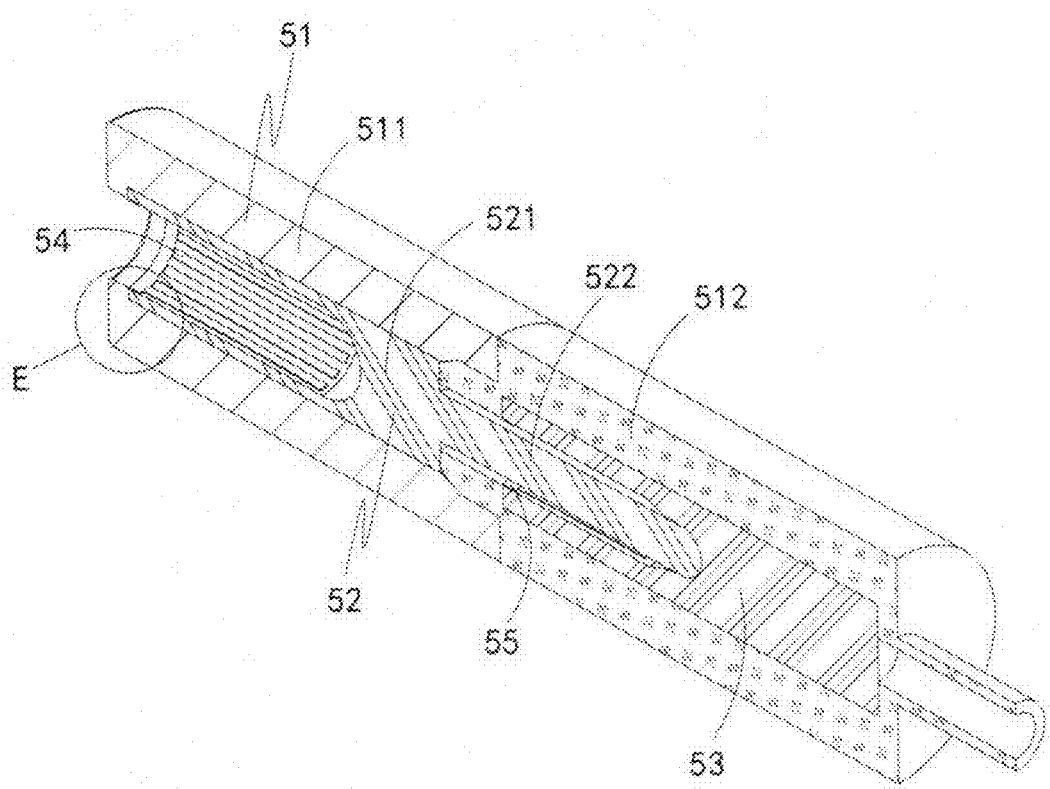
FIG. 17 is a three-dimensional cross-sectional view of a wire connecting head in the Example 7 of the present invention.
Figure 18:
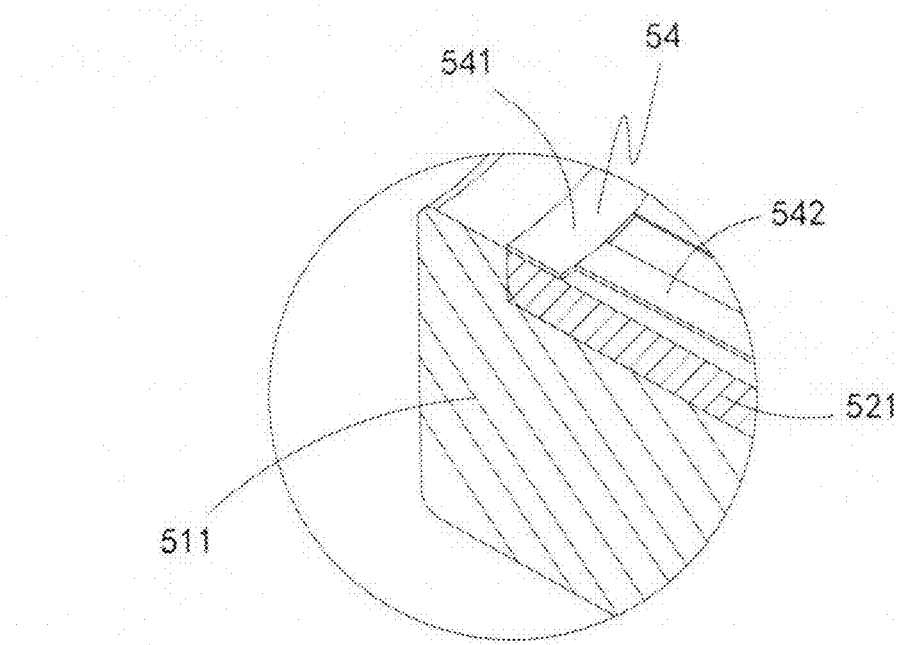
FIG. 18 is an enlarged schematic diagram of E in FIG. 17.

As shown in FIGS. 17 to 18, the differences between this example and Example 1 are as follows: the structure of the wire joint 2 is different. Specifically, the wire joint is called the wire connecting head 5 in this example, and the wire connecting head 5 comprises a joint shell, a joint body 51, a joint rotating body 52, a rotating body joint 53, a lead card 54 and a rotating body contact piece 55; the joint rotating body 52 can be rotated within the joint body 51, and the joint rotating body 52 is provided with a connecting groove for the electrode lead to be inserted; the joint body 51 is provided with a rotating body contact piece 55 which is in an interference fit with the joint rotating body 52; the joint body 51 is made of metal, the joint body 51 comprises a first segment body 511 and a second segment body 512, and the first segment body 511 and the second segment body 512 are detachably connected. In this example, the first segment body 511 and the second segment body 512 are In other embodiments, the two can also be screwed or clamped; in this example, the first segment body 511 and the second segment body 512 are plug-connected, and in other examples, the two can also be screwed or clamped; After the first segment body 511 and the second segment body 512 are plug-connected, the joint shell is sleeved on the outer side of the joint body 51 to ensure the stability of the plug-in connection between the first segment body 511 and the second segment body 512, and also to protect the joint body 51. In this example, the joint shell is cylindrical and divided into left and right arc-shaped bodies along the axis direction, and the left arc-shaped body and the right arc-shaped body are connected by glue, which is a common structure and is well known to those skilled in the art, so it is not shown in the figure; in other examples, the joint shell can also be a rubber film or a silicone film or other insulating materials sleeved outside the joint body 51.

Further, a non-slip structure can be provided between the joint body 51 and the joint shell, for example, a groove is provided on the outer surface of the joint body 51, and a protrusion matching the groove is provided on the inner surface of the joint shell, so that the joint body 51 cannot rotate or move axially relative to the joint shell.

Further, the joint rotating body 52 is made of metal, the joint rotating body 52 comprises a connecting segment 521 and an inserting segment 522; the connecting segment 521 and the inserting segment 522 are provided in an integral structure, and the diameter of the connecting segment 521 is larger than that of the inserting segment 522; the first segment body 511 is provided with a placement slot for placing the connecting segment 521, the second segment body 512 is provided with a rotating body joint 53, and the rotating body joint 53 is provided with an insertion slot for inserting the inserting segment 522. A rotating body contact piece 55 is mounted in the insertion slot. When the joint rotating body 52 is inserted into the insertion slot, the outer surface of the inserting segment 522 will be in close contact with the rotating body contact piece 55 to achieve interference fit; in other examples, the rotating body joint 53 may also be designed as an integrated body with the second segment body 512, that is, the rotating body joint 53 is not provided, and an insertion slot is directly provided on the second segment body 512.

Further, the lead card 54 comprises a retainer ring 541 and an elastic strip 542, the retainer ring 541 is arranged in a ring shape, the connecting segment 521 of the joint rotating body 52 is provided with a connecting groove for insertion of the electrode lead, and the retainer ring 541 is mounted in the connecting groove, located at the opening of the connecting groove in interference fit; the elastic strip 542 is mounted on the retainer ring 541, extending from the side close to the retainer ring 541 to the side away from the retainer ring 541, and the elastic strip 542 is set in an arc-shaped structure, so that the electrode lead and the elastic strip 542 are in an interference fit after the electrode lead is inserted into the connecting groove; the structure of the rotating body contact piece 55 is the same as that of the lead card 54.

Figure 19:
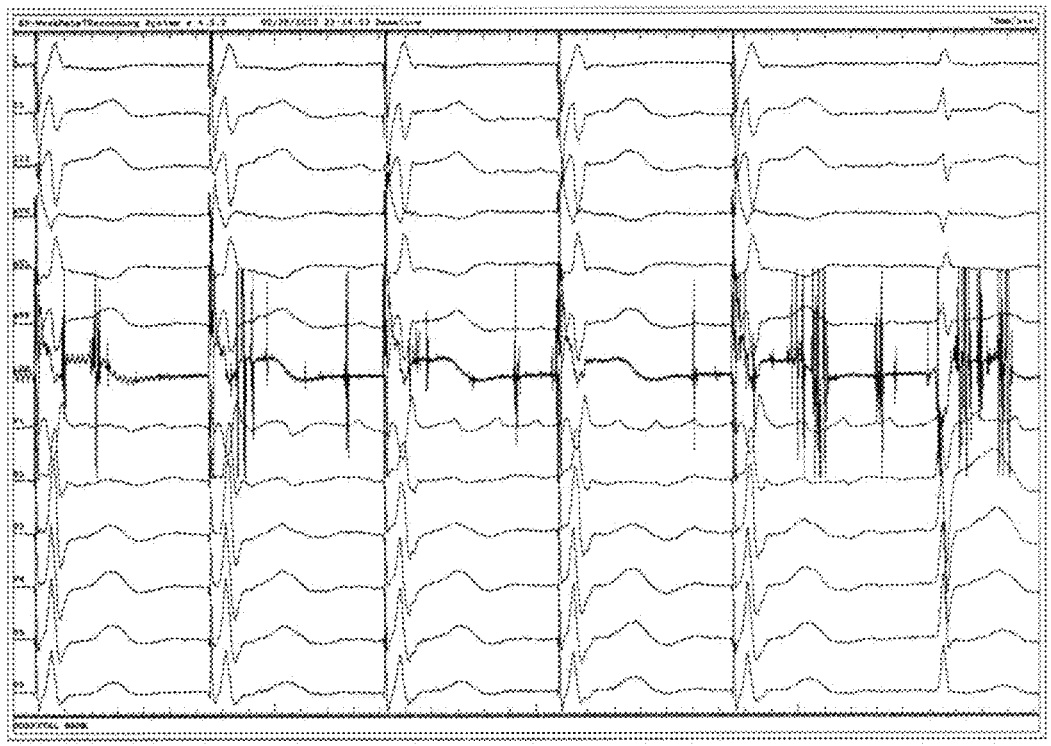
FIG. 19 is an intracavitary electrocardiogram displayed by an ECG monitoring analyzer in the prior art.
Figure 20:
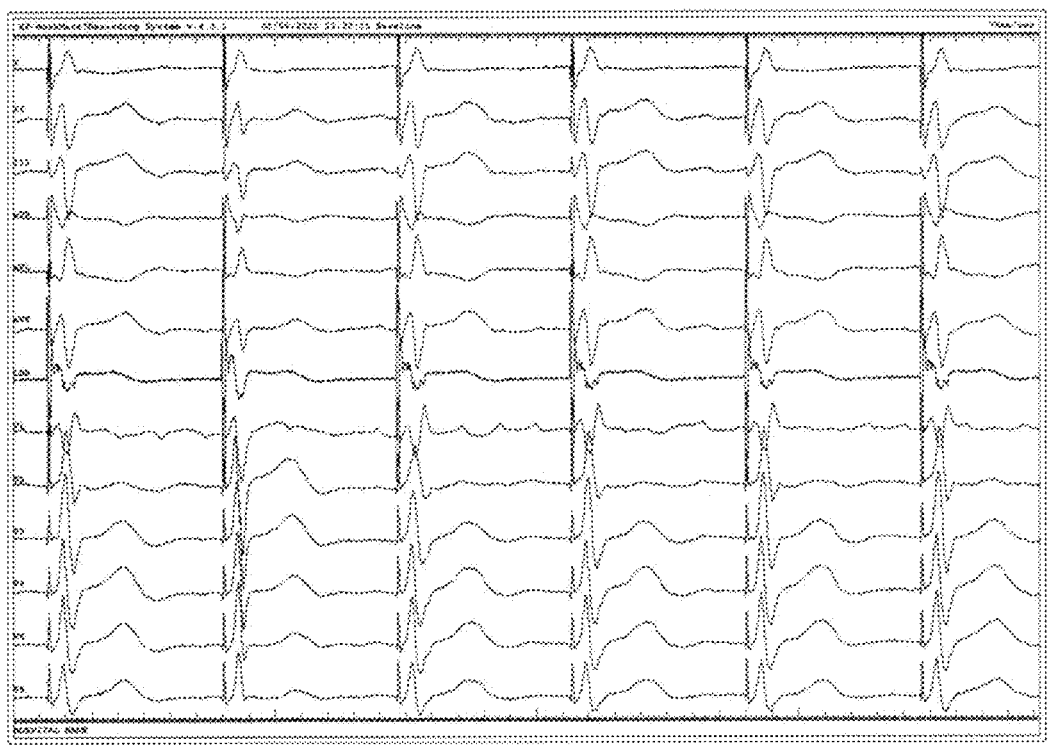
FIG. 20 is an intracavitary electrocardiogram displayed by an ECG monitoring analyzer under the condition of using the connecting wire in Example 7.

Referring to FIGS. 19 and 20, FIG. 19 shows the intracavitary electrocardiogram displayed by an ECG monitoring analyzer in the prior art described in the Background Art, in which there is obvious interference of target signal LBB; FIG. 20 shows the intracavitary electrocardiogram displayed by an ECG monitoring analyzer under the condition of using the connecting wire in this example, in which there is slight interference of target signal LBB.

The preferred embodiments of the present invention have been described in detail above. It should be understood that many modifications and changes can be made according to the concept of the present invention by those skilled in the art without creative efforts. Therefore, any technical solutions that can be obtained by those skilled in the art through logical analysis, reasoning or limited experiments on the basis of the prior art according to the concept of the present invention shall fall within the scope of protection claimed by the appended claims.

What is claimed is:

1. A connecting wire, comprising an electric wire (1) and a wire joint (2) connected to the electric wire (1); wherein the connecting wire further comprise a connecting piece (4) arranged on the electric wire (1), the connecting piece can be simultaneously connected with at least two devices, wherein the wire joint (2) is used for connecting with an electrode lead; when the electrode lead rotates, at least part of the wire joint (2) can rotate with the rotation of the electrode lead and; wherein the wire joint (2) comprises a rotatable head (23) that can rotate back and forth, a rotating connecting portion (231) for connecting with the electrode lead, and a connecting head (24) for connecting the rotatable head (23) and the electric wire (1), the rotating connecting portion (231) is provided on the rotatable head (23).

2. The connecting wire according to claim 1, wherein the connecting piece (4) comprises a wiring portion (43) connected to the electric wire (1), a first connection portion (41) connected to the wiring portion (43), and a second connection portion (42) connected to the wiring portion (43).

3. The connecting wire according to claim 2, wherein the first connection portion (41) is provided with an exposed portion (44) for conducting electricity.

4. The connecting wire according to claim 3, wherein an insertion slot (45) is provided on the second connection portion (42).

5. The connecting wire according to claim 4, wherein the first connection portion (41) on the connecting piece (4) can form a plug fit with the insertion slot (45) on the adjacent connecting piece (4).

6. The connecting wire according to claim 5, wherein a connecting rod (46) is provided in the insertion slot (45), and a connecting hole (47) matched with the connecting rod (46) is provided on the first connection portion (41).

7. The connecting wire according to claim 1, wherein the wire joint (2) further comprises an elastic piece (26) for realizing the anti-disconnection matching of the electrode lead and the rotatable head (23), and the elastic piece (26) is provided in the rotating connecting portion (231).

8. A connecting wire, comprising an electric wire (1) and a wire joint (2) connected to the electric wire (1); wherein at least part of the wire joint (2) can rotate with the rotation of the electrode lead when the electrode lead rotates, wherein the wire joint (2) comprises a rotatable head (23) that can rotate back and forth, a rotating connecting portion (231) for connecting with the electrode lead, and a connecting head (24) for connecting the rotatable head (23) and the electric wire (1), the rotating connecting portion (231) is provided on the rotatable head (23).

9. The connecting wire according to claim 8, wherein the wire joint (2) further comprises an elastic piece (26) for realizing the anti-disconnection matching of the electrode lead and the rotatable head (23), and the elastic piece (26) is provided in the rotating connecting portion (231).

10. The connecting wire according to claim 8, wherein connecting head (24) comprises a connecting column (241), a connecting groove (242) provided on the connecting column (241) and a connecting convex portion (243) provided on the connecting column (241); the electric wire (1) is connected to the connecting groove (242), and the rotatable head (23) is provided with a rotating groove (232) that fits with the connecting convex portion (243).

11. The connecting wire according to claim 10, wherein the rotating groove (232) is formed in a flared structure.

12. The connecting wire according to claim 10, wherein there is a gap between the connecting convex portion (243) and the rotating groove (232).

13. A connecting wire, comprising an electric wire (1) and a wire connecting head (5) connected to the electric wire (1); wherein at least part of the wire connecting head (5) can rotate with the rotation of the electrode lead when the electrode lead rotates, wherein the wire connecting head (5)

comprises a joint body (51) and a joint rotating body (52) arranged in the joint body (51); the joint rotating body (52) can rotate in the joint body (51), and the joint rotating body (52) is provided with a connecting groove for inserting the electrode lead; a rotating body contact piece (55) that is in an interference fit with the joint rotating body (52) is provided in the joint body (51).

14. The connecting wire according to claim 13, wherein the joint rotating body (52) comprises a connecting segment (521) and an inserting segment (522), the diameter of the connecting segment (521) is larger than that of the inserting segment (522).

15. The connecting wire according to claim 14, wherein the connecting segment (521) and the inserting segment (522) are provided in an integral structure.

16. The connecting wire according to claim 13, wherein a lead card (54) is mounted in the connecting groove on the joint rotating body (52), and the lead card (54) is in interference fit with the electrode lead.

* * * * *